(12) United States Patent
Jackson

(10) Patent No.: US 6,379,356 B1
(45) Date of Patent: *Apr. 30, 2002

(54) CLOSURE FOR OPEN ENDED MEDICAL IMPLANT

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 0 days.

This patent is subject to a terminal disclaimer.

(21) Appl. No.: 09/559,157

(22) Filed: Apr. 26, 2000

(51) Int. Cl.[7] .............................................. A61B 17/56
(52) U.S. Cl. ...................................................... 606/61
(58) Field of Search ............................. 606/61, 72, 73, 606/104

(56) References Cited

U.S. PATENT DOCUMENTS

| | | | |
|---|---|---|---|
| 2,243,717 A | * | 5/1941 | Moreira .......................... 606/104 |
| 3,236,275 A | * | 2/1966 | Smith ............................. 606/104 |
| 3,604,487 A | * | 9/1971 | Gilbert ........................... 606/104 |
| 4,484,570 A | * | 11/1984 | Sutter et al. ................... 606/72 |
| 5,005,562 A | | 4/1991 | Cotrel |
| 5,067,955 A | | 11/1991 | Cotrel |
| 5,129,388 A | | 7/1992 | Vignaud et al. |
| 5,154,719 A | | 10/1992 | Cotrel |
| 5,217,497 A | * | 6/1993 | Mehdian ........................ 606/61 |
| 5,257,993 A | | 11/1993 | Asher et al. |
| 5,261,907 A | | 11/1993 | Vignaud et al. |
| 5,261,912 A | | 11/1993 | Frigg |
| 5,346,493 A | | 9/1994 | Stahurski et al. |
| 5,385,583 A | | 1/1995 | Cotrel |
| 5,487,742 A | | 1/1996 | Cotrel |
| 5,562,663 A | | 10/1996 | Wisnewski et al. |
| 5,643,260 A | | 7/1997 | Doherty |
| 5,669,909 A | * | 9/1997 | Zdeblick et al. ............... 606/61 |
| 5,697,929 A | | 12/1997 | Mellinger |
| 5,782,833 A | * | 7/1998 | Haider .......................... 606/61 |
| 6,059,786 A | * | 5/2000 | Jackson ......................... 606/73 |
| 6,077,262 A | * | 6/2000 | Schlapfer et al. .............. 606/61 |
| 6,224,598 B1 | * | 5/2001 | Jackson ......................... 606/61 |
| 6,258,090 B1 | * | 7/2001 | Jackson ......................... 606/61 |

FOREIGN PATENT DOCUMENTS

WO    WO 94/10927    5/1994

* cited by examiner

Primary Examiner—Eduardo C. Robert
(74) Attorney, Agent, or Firm—John C. McMahon

(57) ABSTRACT

A closure for use with an open headed medical implant with a pair of inwardly threaded arms. The closure is lozenge-shaped having a pair of opposed cylindrical sections that have outwardly threaded surfaces that are discontinuous therebetween. The closure also has a central bore receiving a set screw in use. Tools for installing the closure include a tool with a head having a channel receiving the closure and wings on opposite sides of the channel that have outer surfaces that are threaded so as to compliment and complete the threads on the outside of the closure when the tool is thereon so as to provide a continuous circumferential thread for installation.

23 Claims, 3 Drawing Sheets

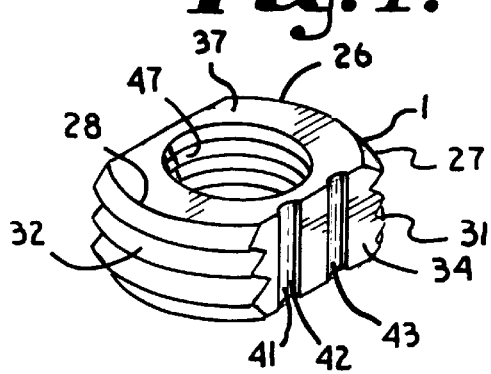
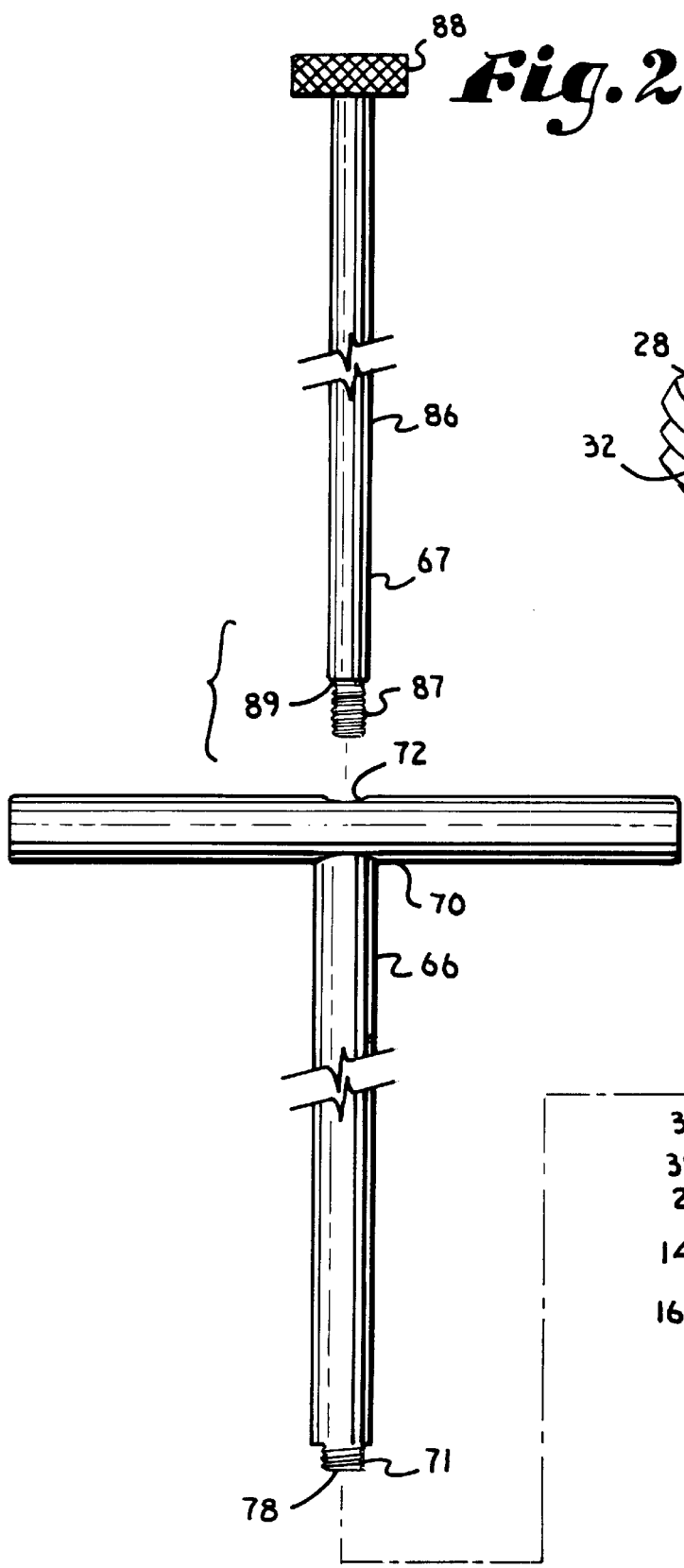
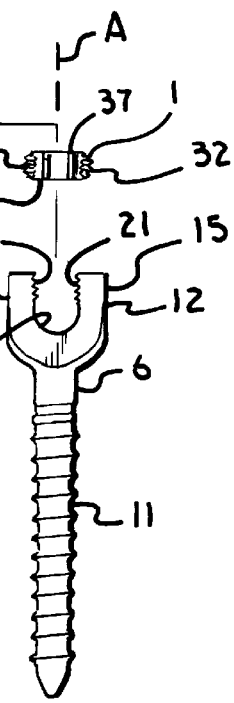

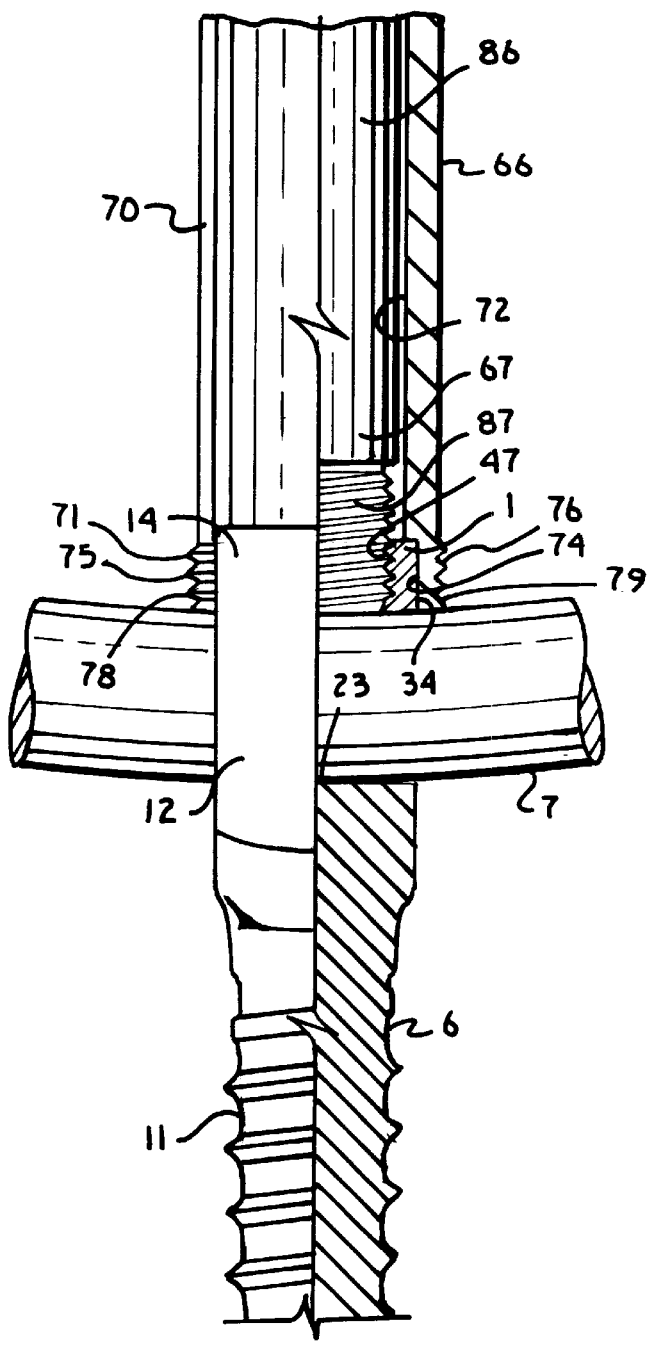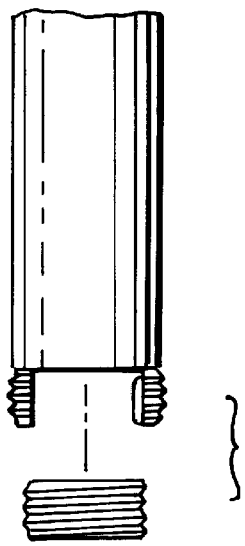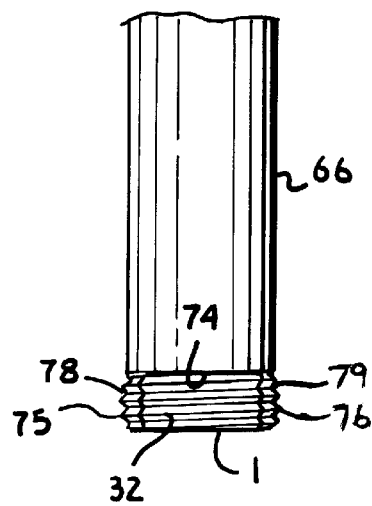

CLOSURE FOR OPEN ENDED MEDICAL IMPLANT

BACKGROUND OF THE INVENTION

The present invention is directed to a closure for use in conjunction with open ended medical implants, such as bone screws, hooks and the like that are used in certain types of spinal surgery. The purpose for the closure is to capture a rod member within the head of the implant and to also lock the captured rod member in position relative to the implant so that the two do not move rotationally or axially with respect to one another.

Medical implants such as bone screws and hooks are used in many types of spinal surgery wherein a structure is built about and within the spine to provide support or strength to diseased, missing or damaged spinal elements of the patient. The implanted apparatus includes a number of different parts which vary with each patient and that are linked together to form a stable support system. For example, bone screws are typically threadably mounted in the bones and have heads that receive rods or similarly shaped connectors that join other bone screws or other elements of the system together.

Bone screws of this type may have either closed heads wherein a rod is threaded into the head from the side or an open head wherein a rod is laid in a channel formed in the head. The later type of bone screws are referred to as open ended bone screws. Such open ended bone screws are favored in many types of spinal surgery, since a rod does not have to be threaded through the bone screw which is difficult to do in the tight space provided and because the spine curves making insertion of a rod that follows the spinal curvature very difficult. On the other hand, the open ended bone screws allow the rod to be laid or drawn into the open channel of the head which greatly simplifies installation in comparison to threading the rod through a head of the bone screw.

While open ended medical implants such as bone screws, hooks and the like are often easier to use in comparison to closed end implants of the same type, the open ended implants do have associated problems. In particular, in open headed implant systems it is extremely important that there be no slippage or relative movement between the connecting rods and the implants, such as bone screws, to which the rods are joined. The rods in this case are usually not linear, but are curved to follow the curvature of the spine. If the rod is allowed to slip either axially or rotate within the bone screw or other connector to which the rod is secured, at a minimum the effectiveness of the implant is decreased and it is possible that the patient could be severely injured. Consequently, it is extremely important to secure the rod to the bone screw or other connector so that no slippage occurs. In some of the prior art devices, open headed implants, which typically have a pair of spaced arms, have been internally threaded and have received a threaded plug between the arms, which plug is designed to abut against the rod under torque and both capture the rod in the head and lock the rod into place.

The plug of the prior art has an outer cylindrical surface that is threaded and is received in the threads of the arms. In order to do this the plug has a comparatively large diameter so that the plug extends out sideways relative to the bone screw or the like or the bone screw must be made wider than is necessary. That is, the plug makes the overall implant wider than is necessary. This presents problems to the surgeon installing the system as space is very limited along the rods in many situations and there is not enough room for all of the total system structure to attach to the rods or, if there is sufficient room for attachment of elements, then there may be insufficient room for the surgeon to manipulate the rod by use of benders to shape the rod to conform to the proper spinal curvature, as is required in many of the surgeries using these devices. It is also noted that other prior art devices have a ring that goes around the outside of the arms. Such a ring is very bulky, taking up a great amount of space along the rods to which the implant is joined. Consequently, it is very desirable to eliminate this side to side extension of the closure along the axis of the rod. That is, it is desirable that the implant and closure both have a low side to side profile.

Secondly, as has been mentioned above, the rods are typically bent throughout the length thereof, such that the rods follow the curvature of the spine. Because of this, the rods seat in the open head of the bone screws and other implants in such a manner that the rod has curvature associated with it, even within the head. When plugs of the prior art seat against the rod, typically the rod is bowed so that the rod engages the plug only at the radially outer edges thereof on both sides. The plug is then torqued against the rod to tighten it down against the seat in the bone screw channel, but it is quite difficult to tighten the rod sufficiently so that the portion of the rod within the head has no curvature after tightening. Subsequently, during use of the device, the rod may be flexed or bent by activity of the person, especially greater activity than normal, such as occurs in an accident or the like, and the remaining curvature of the rod flexes somewhat, thereby loosening the plug. When this occurs, the rod may slip axially or rotate relative to the implant and/or the plug may become loosened and work out of the implant. Both of these situations are very undesirable.

Therefore, there is a need to provide a closure for bone screws and other medical implants having an open head such that the closure has both a relatively thin profile along the axis of the rod or the like and also where the closure has a mechanism whereby the rod can be locked centrally opposite the seat to prevent the rod from becoming loosened should the rod flex during usage.

SUMMARY OF THE INVENTION

A closure is provided for use in conjunction with open headed medical implants, such as bone screws and hooks, which receive rods and other structure for interconnecting with various parts of an overall system. The closure is lozenge shaped with opposed cylindrical sectors that are radially outwardly threaded and that are joined by generally planar surfaces. The threads on the cylindrical sectors are sized and shaped to mate with the threads on internal surfaces of arms of the implants. The closure also includes a central passthrough threaded bore that is coaxially located with respect to the closure.

A set screw having a base with a radially outward threaded surface and a head is threadably mounted in the bore during installation of the closure. The set screw includes a point that extends from the closure bore when fully installed so as to engage a rod member located in the head of the implant. The set screw may be of a break-off head variety or may retain its head after installation. Also the set screw may be designed to rotate with the closure during installation or independently of the closure. In one embodiment the set screw is designed to extend entirely through the bore of the closure during installation and engage a rod in an implant head under torque until the head of the set screw breaks away at a predetermined torque. In such an embodiment the closure functions to capture the rod in the head and the set screw functions to lock the rod in place relative to the head of the implant.

A set of tools is also provided for installation of the closure since the closure has discontinuous threads thereon. The installation tool includes a handle for rotating and a head that has a channel for receiving the closure. The head also has a pair of wings on either side of the channel which are radially outward threaded and positioned so as to mate with the closure such that the threads on the closure and the threads on the wings form a generally continuous thread that is sufficient to allow the structure to be threadedly mated without cross threading or having thread turns at different levels on the arms mate with a single thread on the closure and that may be utilized advantageously to mount the closure in the head of the implant. A second tool including a shaft with a threaded tip may also be mounted in the bore of the closure during installation to allow the installer to better grip the closure.

OBJECTS AND ADVANTAGES OF THE INVENTION

Therefore, the objects of the present invention are: to provide an overall medical implant system wherein the system includes various bone screws, hooks and the like with open heads that are joined with a series of rod-like structures by use of a closure in accordance with the present invention; to provide such a closure which is relatively thin in profile along the axes of the rods with which it is utilized; to provide such a closure which is lozenge shaped and includes a pair of cylindrical sectors that are opposed to one another and which are externally threaded so that the closure is only partially threaded and such that the thread is discontinuous between the sectors, but in such a way as to threadably mate with threads on internal surfaces of arms of open headed implants; to provide such a closure which includes a central passthrough and threaded bore; to provide such a closure with such a bore in conjunction with a threaded set screw received in the bore and passing at least partially through the bore during installation; to provide such a closure wherein the closure captures a rod member within a head of an implant and wherein the set screw locks the rod member in place relative to the implant head to prevent rotation or axial relative movement of the rod member in relation to the head; to provide such a closure having a relatively thin profile upon installation; to provide a set of tools to be used in conjunction with installation of the closure; to provide such tools including a closure installation tool having a head that receives the closure and a pair of wings that extend outwardly on either side of the closure with threads on outer surfaces of the wings that compliment threads on the closure so as to provide, when joined, a substantially continuous thread for use in installation of the closure; to provide such an overall system and, especially, a closure that is relatively easy to use, economical to produce and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a closure in accordance with the present invention.

FIG. 2 is an exploded side elevational view of a bone screw, a closure and a pair of closure installation tools utilized in installation of the closure in the bone screw.

FIG. 3 is a side elevational view of the closure and a fragmentary view of one of the closure installation tools just prior to joining together thereof.

FIG. 4 is a side elevational view similar to FIG. 3 showing the closure and a fragmentary portion of the closure installation tools with the closure received therein.

FIG. 5 is a side elevational view of a medical implant system including the bone screw, a rod and the closure with the closure installing tools thereon and with the closure being installed in a head of the bone screw, with portions broken away to show detail thereof.

DETAILED DESCRIPTION OF THE INVENTION

Figure 6:
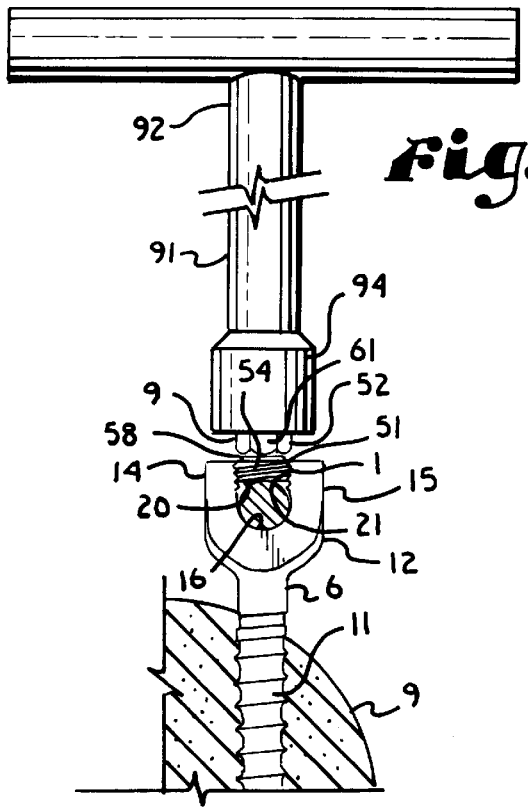
FIG. 6 is a fragmentary side elevational view of the bone screw mounted in a vertebrae and with the closure capturing a rod therein and still further with a set screw being installed in the closure with a torquing tool.
Figure 8:
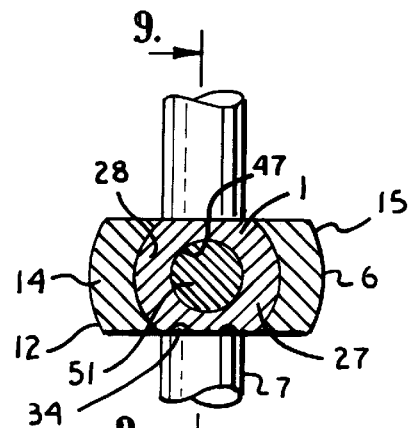
FIG. 8 is a cross-sectional view of the implant, the rod, the closure and the base of the set screw, taken along line 8—8 of FIG. 7.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a closure in accordance with the present invention. The closure 1 is utilized in conjunction with a bone screw 6 that receives a rod 7 and is implanted in a vertebrae 8 of a patient's spine. The closure 1 is locked with respect to the bone screw by a set screw 9.

The bone screw 6 is conventionally referred to as an open headed bone screw having a threaded shank 11 that is screwed into a patient's vertebrae 8 and a head 12. The bone screw head 12 is bifurcated with a pair of upstanding and spaced arms 14 and 15 forming a channel 16 therebetween with a seat 17 at the bottom of the channel 16.

Radially internal surfaces 20 and 21 of the arms 14 and 15 respectively are threaded. The closure 1 of the present invention may be used in conjunction with any of a number of different types of open headed implants, including the illustrated bone screw, hooks or the like which are conventionally used in spinal surgery.

The rod 7 is circular in cross section and elongate, although it is foreseen that rods of other cross section including square may be used with the invention. The rod 7 may also be smooth surfaced or knurled. The rod 7 illustrated in the figures is somewhat curved so as to be upwardly concave when viewed from the side, such as in FIG. 5 or 9. Because the rod 7 is curved, it often does not lie flat in the seat 17, but rather has a primary point of contact 23 that engages the seat 17. In certain embodiments, the rod may engage the seat 17 at more than one location. It is also seen that in accordance with the present invention the closure 1 could be used in conjunction with other rod-like connector structures to maintain such structures in the head of the bone screw 6.

The closure 1 has a plug or body 26 that is lozenge-shaped having a pair of generally equal and opposed cylindrical sections 28 and 29 on either end thereof. Each of the cylindrical sectors 28 and 29 have radially outward surfaces 31 and 32 respectively that are threaded. The threads of the surfaces 31 and 32 are discontinuous with respect to one another, such that there is no continuous thread associated with the exterior of the closure 1 itself which extends entirely about the closure 1. Joining the curved surfaces 31 and 32 are a pair of generally planar surfaces 34 and 35. The closure 1 also has a generally flat upper surface 37 and lower surface 38 which are perpendicular with respect to an axis of rotation A of the closure 1. The threads of the curved outward surfaces 31 and 32 are threadably mateable with the threads on the arm surfaces 20 and 21 respectively except that it is very difficult to do so without the assistance of the tool described below.

One of the planar surfaces 34 includes a guide 41 for facilitating installation of the closure 1. In the illustrated embodiment the guide 41 comprises a pair of spaced grooves 42 and 43 extending from top to bottom of the closure 1.

The closure 1 includes a central bore 47 that is coaxial with the axis A of rotation of the closure 1 and that is internally threaded. The bore 47 passes entirely through the closure 1 and extends between the upper surface 37 and lower surface 38.

Figure 7:
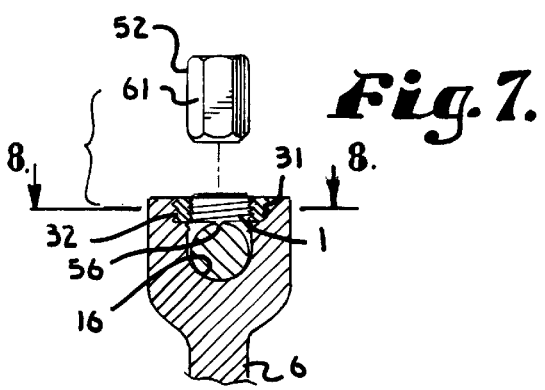
FIG. 7 is a side elevational view of the bone screw, the rod and the closure of FIG. 6 with a head of the set screw separated from a base thereof subsequent to torquing of the set screw, and with portions broken away to show detail thereof.

The set screw 9 has a base 51 and a head 52. The base 51 has a radially outward surface 54 that is threaded so as to be mateable with the thread in the bore 47. The base 51 also has a lower and outwardly projecting point 56 that during and after installation is coaxial with the axis A. The set screw base 51 and head 52 are joined by a break-away region 58, such that the base 51 breaks away from the head 52, when a predetermined torque is applied to the set screw 9, such as is illustrated in FIG. 7. The head 52 includes a grippable surface 61 having a number of polyhedrally arranged faces for gripping by a tool described below.

A closure installation tool 66 and a closure holding tool 67 are provided for installing the closure 1. The closure installation tool 66 includes a T-shaped handle 70 and a head 71. A bore 72 runs through the interior of the handle 70 and head 71 for receiving the holding tool 67 and is sized to slidingly receive the holding tool 67 therein.

The head 71 includes a channel 74 sized and shaped to snugly receive the closure 1. FIG. 3 shows the closure 1 just prior to being received in the tool head 71 and FIG. 4 shows the closure 1 received in the tool channel 74. The head 71 also includes a pair of wings 75 and 76 that are positioned on opposite sides of the channel 74. An outer surface 78 and 79 of each wing respectively is threaded and the wings 75 and 76 are sized and shaped such that the threads on the surfaces 78 and 79 compliment and generally complete the threads on the closure surfaces 31 and 32, so that the threads on the radially outward portions of the closure 1 are thereby completed and made substantially continuous by installation of the closure installation tool 66 on the closure 1. In the manner the closure 1 can be easily screwed into the bone screw head 12 between the arms 14 and 15. An inner wall 82 of the channel 74 includes a pair of tongues 83 that are aligned to mate with the grooves 42 and 43 of the closure 1, when the closure 1 is placed in the installation tool 66 to insure that the closure 1 is properly aligned with the tool 66 and that the threads of the tool 66 are positioned on the correct sides of the closure 1, since the threads on opposite sides are not interchangeable.

The holding tool 67 comprises a shank 86 joined to a threaded tip 87 at a shoulder 89 and a turning knob 88. The tip 87 is sized and shaped to be threadably received in the closure bore 47. In particular, the holding tool 67 is inserted through the closure installation tool bore 72, as is seen in FIG. 5 and secured to the closure 1 so as to hold the closure 1 in the closure installation tool channel 74, such that the closure tool 66 completes the threads on the exterior of the closure 1. The closure 1 is then threaded into the bone screw head 12 as is seen in FIG. 5. FIG. 5 shows this process near the end of the installation of the closure 1. Normally, the closure 1 is, not torqued tightly against the rod 7, but is mainly used to capture the rod 7 within the head 12. It is possible for the closure 1 to be tightened tightly to lock the rod 7 and bone screw 6 together in some uses, but locking is normally provided by the set screw 9.

Once the closure 1 is installed, as is seen in FIG. 5, the tools 66 and 67 are removed and the set screw 9 is inserted into the bore 47. A third tool 91 for torquing is then utilized to rotate the set screw 9. The torquing tool 91 includes a turning handle 93 and a socket-type head 94 that is mateable with the set screw grippable surface 61 to allow torque to be applied to the set screw 9 by turning the tool 91. Normally the set screw 9 would be torqued to a torque sufficient to lock the rod 7 relative to the remainder of the bone screw 6. For example, the set screw 9 may be torqued to 100 inch pounds of torque, although the exact torque may vary with the particular procedure or parts being used.

Figure 9:
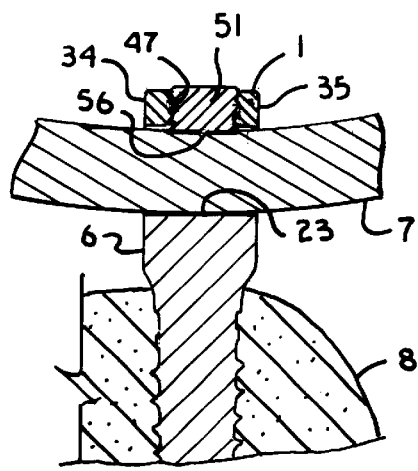
FIG. 9 is a cross-sectional view of the vertebrae, bone screw, the rod, the closure and the set screw, taken along line 9—9 of FIG. 8.

In the illustrated embodiment the set screw 9 is a breakaway head type set screw wherein the head 52 breaks away from the base 51 at a preselected torque. This is seen in FIG. 7. Once the head 52 breaks away from the base 51, the installation is considered to be complete. Preferably, the base 51 includes the point 56 that engages the rod 7. Also preferably the point 56 engages the rod 7 opposite the point of contact 23 of the rod with the seat 17, as is seen in FIG. 9. It is foreseen that a non-breakaway head type screw may also be used in conjunction with the invention, but a breakaway head set screw provides a lower profile to the completed implant system. The set screw base 52 may also include one or more bores or the like (not shown) to allow the base 51 to be removed after the head 52 is broken away.

Normally, the closure 1 is removed from the bone screw 6 by re-mounting the closure installation tool 66 over the closure 1 and unscrewing the closure 1. However, as noted in the last paragraph, it is also possible to have a removable set screw with a head or other gripable structure to allow it to be removed and the closure 1 may then be removed more easily with the tool 66 or another tool.

The term "continuous" when used herein in conjunction with the term "thread" is meant to describe a thread that is sufficiently complete to allow the structure to which the thread is attached to be readily screwed into a full or partial receiving thread and may include small or slight gaps.

It is to be understood that while certain forms of the present invention have been illustrated and described herein, it is not to be limited to the specific forms or arrangement of parts described and shown.

What is claimed and desired to be secured by Letters Patent is as follows:

1. A closure for an open ended medical implant having a pair of spaced and internally threaded arms; said closure comprising:
   a) a closure body having a truncated cylindrical shape with at least one sector removed;
   b) said body having a radially outer surface that is threaded with a discontinuous thread; said thread being sized, shaped and positioned to threadably mate with threaded arms associated with an implant.

2. The closure according to claim 1 wherein:
   a) said body has a pair of equal and opposite sectors removed.

3. A closure for an open ended medical implant; said closure comprising;
   a) a closure body having a pair of opposed cylindrical sectors with each of said sectors having radially outward curved surfaces with threads thereon sized and shaped to threadably mate with threads of the medical implant; said sector threads being discontinuous with each other.

4. The closure according to claim 3 wherein:
   a) said closure body includes a central pass through and coaxial threaded bore.

5. A closure and tool combination comprising:
   a) a truncated cylindrical body with spaced sectors having threads on outer surfaces thereof and with said threads being discontinuous between said sectors; and
   b) an installation tool having a handle for rotating and a head; said head receiving said body and having spaced wings that are positioned on opposite sides of said body when received in said head; said wings having outer surfaces that are threaded and compliment the threads of said body sectors so as to form a continuous thread about said body for facilitating installation of said body.

6. The combination according to claim 5 wherein:
   a) said tool wings cooperate with said body to form a cylindrical structure with said continuous external thread thereon.

7. The combination according to claim 5, wherein:
   a) said body includes a central bore; and including
   b) a second holding tool having a handle and a threaded tip adapted to be received in said bore to facilitate handling during installation.

8. A closure for an open ended medical implant having a pair of spaced and internally threaded arms; said closure comprising:
   a) a closure body having a thread on a radially outward facing surface; said body thread sized and located to be adapted to mate with internal threads on the implant arms;
   b) said body having a central threaded bore;
   c) said body being cylindrical in shape except with opposed equal segments removed such that the body thread is discontinuous; and
   d) a threaded set screw sized and shaped to be received in said threaded bore in use.

9. The closure according to claim 8 wherein:
   a) said body has generally parallel and spaced walls joining opposite ends of said body outward facing surfaces.

10. The closure according to claim 9 wherein:
    a) at least one of said walls includes a guide.

11. The closure according to claim 8 in combination with a complimenting installation tool; said tool including:
    a) a handle for turning by a user;
    b) a head having a channel sized and shaped to receive said closure body; said head also having a pair of externally threaded wings located on either side of said channel and having threads sized and positioned to compliment threads on said closure to form a continuous thread when joined, such that said closure is screwable into an implant.

12. The closure and tool combination of claim 11 wherein:
    a) said closure includes a first part of a guide and said tool includes a second part of a guide to ensure said closure and tool are correctly aligned during installation of said closure on an implant.

13. A closure for an open ended medical implant having a pair of spaced and internally threaded arms; said closure comprising:
    a) a closure body having a thread on a radially outward facing surface; said body thread sized and located to be adapted to mate with internal threads on the implant arms;
    b) said body thread being in two opposed equal portions extending in total substantially less than 360° about said body;
    c) said body having a central threaded bore; and
    d) a threaded set screw sized and shaped to be received in said threaded bore in use.

14. A closure for an open ended medical implant having a pair of spaced and internally threaded arms; said closure comprising:
    a) a closure body having a thread on a radially outward facing surface; said body thread sized and located to be adapted to mate with internal threads on the implant arms;
    b) said body having a central threaded bore;
    c) a said body being lozenge-shaped; and
    d) a threaded set screw sized and shaped to be received in said threaded bore in use.

15. A closure for an open ended medical implant having a pair of spaced and internally threaded arms; said closure comprising:
    a) a closure body having a truncated cylindrical shape with at least one sector removed;
    b) said body having a radially outer surface that is threaded with a discontinuous thread that is sized and shaped to threadably mate with the threaded arms of the implant in use; and
    c) said body being lozenge-shaped.

16. A closure for an open ended medical implant having a pair of spaced and internally threaded arms; said closure comprising:
    a) a closure body having a truncated cylindrical shape with at least one sector removed;
    b) said body having a radially outer surface that is threaded with a discontinuous thread;
    c) said body having a pair of equal and opposite sectors removed;
    d) said body including an axially extending pass through and threaded bore; and further including
    e) a set screw being sized and shaped to be operably received in said bore during use.

17. A medical implant system comprising:
    a) a medical implant having an open channel positioned between a pair of arms and being sized and shaped to receive a rod member; said arms being spaced and having threaded internal facing surfaces;

b) a closure body having a radially outward threaded surface; said closure body having an axially aligned pass through threaded bore;

c) said closure body threaded surface being discontinuous; and d) a threaded set screw operably received in said bore during installation and being sized and shaped to have a tip extending from said bore when fully installed.

18. The implant system according to claim 17 wherein:

a) said medical implant is a bone screw.

19. A medical implant system comprising:

a) a medical implant having an open channel positioned between a pair of arms and being sized and shaped to receive a rod member; said arms being spaced and having threaded internal facing surfaces;

b) a closure body having a radially outward threaded surface; said closure body having an axially aligned pass through threaded bore;

c) said closure body including two opposed sectors of a cylinder with a radially outward surface of each of said sectors being threaded so as to be mateable with the threads of said arm facing surfaces; and d) a threaded set screw operably received in said bore during installation and being sized and shaped to have a tip extending from said bore when fully installed.

20. The implant system according to claim 19 including:

a) a pair of generally planar surfaces extending between opposite sides of said closure body sectors.

21. The implant system according to claim 20 wherein:

a) at least one of said planar surfaces includes an orientation guide thereon.

22. The implant system according to claim 21 wherein:

a) said orientation guide comprises a top to bottom groove.

23. A medical implant system in combination with a closure installation tool comprising:

a) a medical implant having an open channel positioned between a pair of arms and being sized and shaped to receive a rod member; said arms being spaced and having threaded internal facing surfaces;

b) a closure body having a radially outward threaded surface; said closure body having an axially aligned pass through threaded bore;

c) a threaded set screw operably received in said bore during installation and being sized and shaped to have a tip extending from said bore when fully installed; wherein the tool includes:

d) a handle for turning by a user;

e) a head coaxially attached to said handle; said head including a channel for snugly receiving said closure body and a pair of wings on opposite sides of said channel; each of said wings having a radially outward surface with a thread thereon; said wing threads and said closure body threads cooperating to form a complete circumferential thread to facilitate installation of said closure body in said implant.

* * * * *